(12) United States Patent
Stamler et al.

(10) Patent No.: US 8,075,922 B2
(45) Date of Patent: Dec. 13, 2011

(54) METHOD OF CO-INFUSING A DEOXYGENATED HEMOGLOBIN CONTAINING BLOOD SUBSTITUTE AND INORGANIC NITRITE

(75) Inventors: Jonathan S. Stamler, Chapel Hill, NC (US); David J. Singel, Bozeman, MT (US)

(73) Assignees: Montana State University-Bozeman, Bozeman, MT (US); Duke University, Durham, NC (US)

( * ) Notice: Subject to any disclaimer, the term of this patent is extended or adjusted under 35 U.S.C. 154(b) by 1093 days.

(21) Appl. No.: 10/538,404

(22) PCT Filed: Dec. 10, 2003

(86) PCT No.: PCT/US03/37081
§ 371 (c)(1),
(2), (4) Date: Jun. 21, 2006

(87) PCT Pub. No.: WO2004/054433
PCT Pub. Date: Jul. 1, 2004

(65) Prior Publication Data
US 2006/0252671 A1    Nov. 9, 2006

Related U.S. Application Data

(60) Provisional application No. 60/432,616, filed on Dec. 12, 2002.

(51) Int. Cl.
*A01N 59/00* (2006.01)
*A61K 38/41* (2006.01)
*A61K 38/00* (2006.01)
*A61K 38/06* (2006.01)

(52) U.S. Cl. .... 424/718; 514/13.4; 514/13.5; 514/21.92

(58) Field of Classification Search .................. None
See application file for complete search history.

(56) References Cited

U.S. PATENT DOCUMENTS

| | | | |
|---|---|---|---|
| 4,820,269 A * | 4/1989 | Riddell | ........................... 604/85 |
| 6,124,255 A | 9/2000 | Schlag et al. | |
| 6,291,424 B1 | 9/2001 | Stamler et al. | |

FOREIGN PATENT DOCUMENTS

| | | | |
|---|---|---|---|
| WO | WO 96/30006 | * | 10/1996 |
| WO | WO-97009972 A1 | | 3/1997 |
| WO | WO-98/34955 A1 | | 8/1998 |
| WO | WO-99/01146 A1 | | 1/1999 |
| WO | WO 01/09616 | | 2/2001 |
| WO | WO-03102575 A1 | | 12/2003 |

OTHER PUBLICATIONS

Nelle et al., "Effects of red cell transfusion on cardiac output and blood flow velocities in cerebral and gastrointestinal arteries in premature infants", Archives of Disease in Childhood. Fetal and Neonatal Edition, 71 (1) : F45-8 (1994).*
Carson et al., "Perioperative Blood Transfusion and Postoperative Mortality", JAMA 279 (3) : 199-205 )1998).*
Engoren et al., "Long-term survival in the Intensive Care Unit after Erythrocyte Blood Transfusion", American J. Critical Care : an official pulication, America Assoc. of Critical-Care Nurses 18 (2) : 124-31 (2009), abstract only.*
Remy et al., "Modified hemoglobins: Contributions and perspectives", Schweizerische Medizinische Wochemschrift 127 (25):1088-1096 (1997), abstract only.*
Johnson III et al., "Cardioprotective Effects of Acidified Sodium Nitrite in Myocardial Ischemia with Reperfusion", Journal of Pharmacology and Experimental Therapeutics 252 (1) : 35-41 (1990).*
Jaening et al., Uber die Reaktion zwischen Natriumnitrit and Hemoglobin IV. Umsetzung in Abwesenheit von Sauerstoff. Acta Biologica et Medica Germanica (1970), vol. 25, No. 2, pp. 355-358.
Alayash et al., "Hemoglobin-based blood substitutes: oxygen carriers, pressor agents, or oxidants?", Nature Biotechnology, 17:545-549 (1999).
Reiter et al., "Cell-free hemoglobin limits nitric oxide bioavailability in sickle cell disease", Nature Medicine, 8(12): 1383-1389 (2002).

* cited by examiner

*Primary Examiner* — Sandra Saucier
(74) *Attorney, Agent, or Firm* — Mintz Levin Cohn Ferris Glovsky and Popeo, P.C.; Ivor R. Elrifi; Matthew Pavao

(57) ABSTRACT

Contrary to current opinion that nitrite in general oxidizes hemoglobin with elimination of active nitric oxide, deoxygenated hemoglobin reacts with low concentration inorganic nitrite to produce very stable iron nitrosyl hemoglobin which on delivery into the body is converted to a hemoglobin capable of nitric oxide delivery and provides vasodilator and antiplatelet activity. This provides basis for ameliorated risk blood product transfusions.

7 Claims, 1 Drawing Sheet

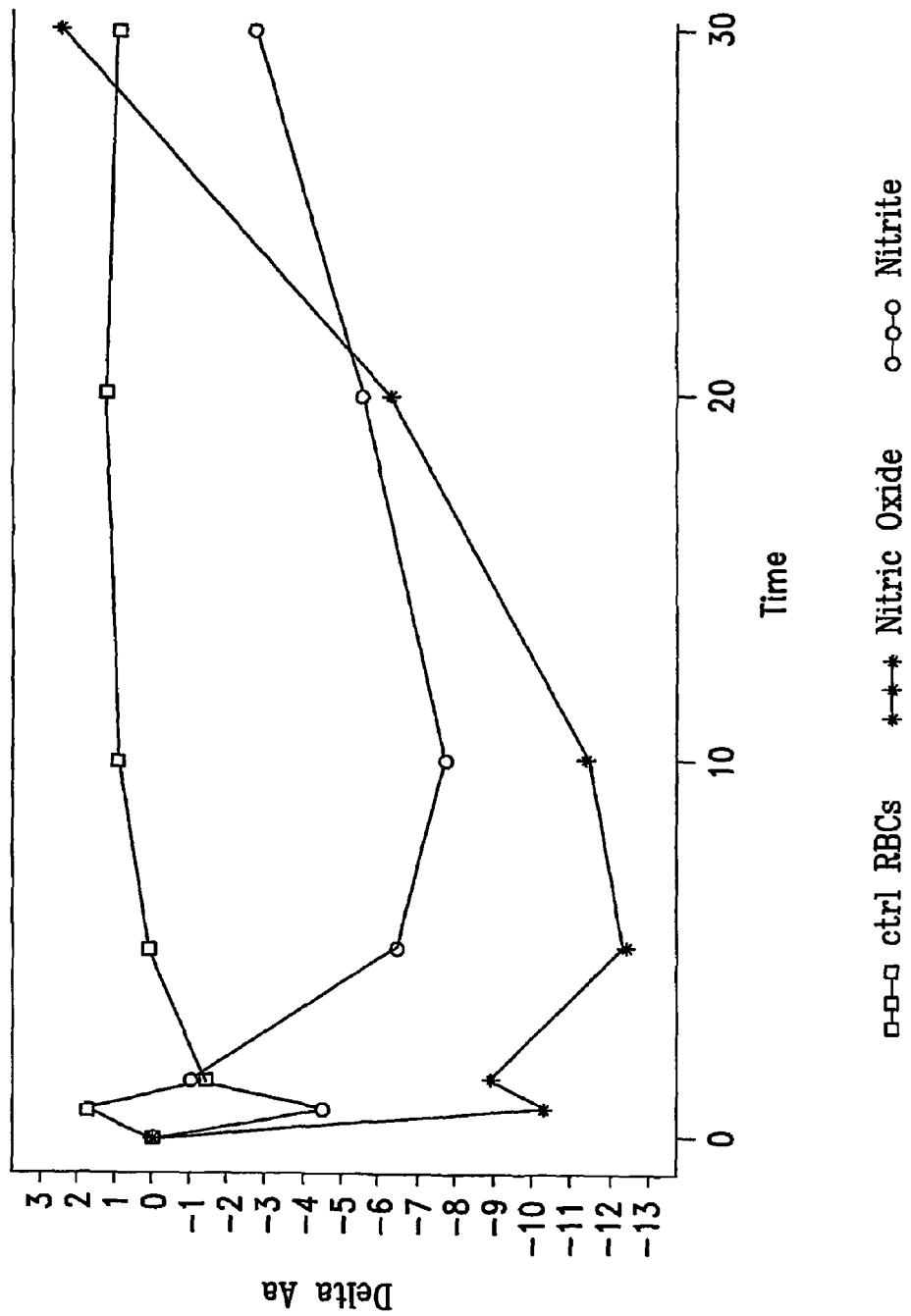

METHOD OF CO-INFUSING A DEOXYGENATED HEMOGLOBIN CONTAINING BLOOD SUBSTITUTE AND INORGANIC NITRITE

CROSS-REFERENCE TO RELATED APPLICATIONS

This application claims the benefit of U.S. Provisional Patent Application No. 60/432,616, filed Dec. 12, 2002.

The invention was made at least in part with United States Government support under National Institutes of Health Grant Nos. HL52529, HL59130 and HL66179-02 and National Science Foundation Grant No. MCB00981228. The United States Government has certain rights in the invention.

TECHNICAL FIELD

The invention herein is directed in one case to mitigating transfusion risk and in another case to providing a red blood cell or hemoglobin based therapeutic.

BACKGROUND OF THE INVENTION

It is known that patients undergoing transfusions of blood substitutes, hemoglobins and red blood cells have increased morbidity and/or mortality rate. It has been posited that this increased morbidity and/or mortality is the result of excess scavenging of nitric oxide causing constricting of blood vessels. While S-nitrosylated hemoglobin (SNO-Hb) is known to be a vasodilator, it is not usefully used in blood substitutes or transfusions, in significant part, because it is unstable, that is it cannot be readily stored without deteriorating. Thus, there is motivation to generate alternative and stable and bioactive preparations, that is morbidity ameliorating preparations.

SUMMARY OF THE INVENTION

It has been discovered herein that inorganic nitrite can mediate formation of iron-nitrosyl hemoglobin which is very stable and is oxygenated in the body to form SNO-Hb with vasodilator and anti-platelet activity, i.e., inorganic nitrite reaction to form iron nitrosyl hemoglobin creates a molecule which upon delivery into the body is endowed with vasodilator and antiplatelet activity and is functional to mitigate transfusion increased morbidity and mortality risks and to mitigate morbidity risk associated with hemoglobin and red blood cells based therapeutics and that the iron nitrosyl hemoglobin can be formed by nitrite incubation with deoxyhemoglobin at low nitrite to hemoglobin ratios, which upon oxygenation generates SNO-Hb.

Hemoglobin is a tetramer constituted of two α-subunits and two β-subunits. In human hemoglobin, each subunit contains one heme while the β-subunits also contain highly reactive SH (thiol) containing groups (β-cys93). It has been thought that nitrite is an oxidant of hemoglobin and that the consequence of nitrite reaction with hemoglobin is the elimination of the nitrite by conversion to nitrate or by complexing the nitric oxide (NO) derived upon oxidation to α-subunit ferrous hemes which quench nitric oxide bioactivity. It has been discovered herein that low (physiological) concentrations of nitrite do not oxidize oxyhemoglobin as thought but instead combine with deoxygenated hemoglobin to store NO on heme β-subunit of hemoglobin tetramer to form iron nitrosyl hemoglobin and upon oxygenation the NO is transferred from the heme of β-subunits to thiol of β-cys93 to produce SNO-Hb.

One embodiment of the invention herein, denoted the first embodiment, is directed to a method for preparing a stable iron nitrosylated hemoglobin readily convertible to SNO-hemoglobin, comprising the step of reacting low concentration of inorganic nitrite with deoxyhemoglobin (1:10 to 1:1000 mole ratios of nitrite to deoxyhemoglobin) to form iron nitrosyl hemoglobin which is a very desirable product because it is stable and upon oxygenation generates a hemoglobin product capable of NO delivery, e.g., SNO-Hb.

Another embodiment of the invention herein, denoted the second embodiment, is directed to a method of blood product transfusion into a human patient in need of blood product transfusion, with decreased morbidity and/or mortality risk, comprising the steps of incubating inorganic nitrite and blood substitute or red blood cells or blood hemoglobin or combination of two or more thereof, comprising deoxygenated hemoglobin, the mole ratio of nitrite to deoxygenated hemoglobin ranging from 1:10 to 1:1000, to form blood substitute or red blood cells or hemoglobin or combination product, comprising iron nitrosyl hemoglobin, and transfusing the product comprising iron nitrosyl hemoglobin into the human patient.

Still another embodiment of the invention herein, denoted the third embodiment, is directed to a method of blood product transfusion into a human patient in need of a blood product transfusion, with decreased morbidity and/or mortality risks from the transfusion compared to a conventional transfusion, comprising the steps of a co-infusing blood substitute or red blood cells at the rate of 1 to 250 cubic centimeters per hour and inorganic nitrite at the rate of 0.01 to 10 micromoles per minute.

Still another embodiment of the invention herein, denoted the fourth embodiment, is directed to stored blood, stored blood substitute, stored red blood cells, stored hemoglobin or stored combination of two or more thereof in admixture with nitric oxide or after inorganic nitrite pretreatment, for use at a later time, and to a method of providing composition for transfusion for use at a later time, comprising storing composition comprising blood, blood substitute, red blood cells, blood hemoglobin or combination of two or more thereof in admixture with nitric oxide or after inorganic nitrite pretreatment, to preserve function and any red blood cells.

Still another embodiment of the invention herein, denoted the fifth embodiment, is directed to a method of treating a patient in need of nitric oxide therapy comprising administering red blood cells or blood hemoglobin based therapeutic obtained by incubating red blood cells or blood hemoglobin, comprising deoxygenated hemoglobin, with inorganic nitrite, the mole ratio of nitrite to deoxygenated hemoglobin ranging from 1:10 to 1:1000, whereby the therapeutic contains iron nitrosyl hemoglobin.

The mortality rate from blood transfusions is considered to be increased, and both blood transfusions and hemoglobins as well as erythropoietin (which increases hemoglobins) commonly increase blood pressure and pulmonary pressure and may decrease tissue perfusion. The invention of the second and third embodiments decreases this mortality rate and the aforedescribed morbidity.

The term "deoxygenated hemoglobin" is used herein to mean a hemoglobin molecule carrying an average of less than three oxygens. Deoxygenation of hemoglobin provides deoxyhemoglobin which is deoxygenated, that is carries less oxygen.

The term "iron nitrosyl hemoglobin" is used herein to mean nitric oxide bound to heme iron of β-subunit of hemoglobin.

The term "oxygenation" is used herein to mean introduction of oxygen.

The term "blood product" is used herein to mean composition comprising red blood cells, blood hemoglobin or combination thereof.

The term "blood substitute" is used herein to mean a substitute for blood comprising hemoglobin.

The term "incubating" is used herein to mean to maintain under conditions favorable to reaction and "co-incubating" is used herein to mean maintaining more than one compound under such conditions.

The term "co-infusion" is used herein to mean infuse contemporaneously, or carrying out one infusion shortly before or shortly after another.

The term "red blood cells or blood hemoglobin based therapeutic" is used herein to mean an amount of red blood cells or blood hemoglobin insufficient to significantly raise average hemoglobin level (i.e., insufficient to raise average hemoglobin level at least 10%), but raises nitric oxide level in blood significantly, i.e., by at least 10%.

BRIEF DESCRIPTION OF THE DRAWING

FIG. 1 is a graph of time versus alveolar-arterial gradient in swine for nitric oxide (asterisks), nitrite (circles) and control (squares) and shows results of Background Example 2. In FIG. 1, Delta Aa means alveolar-arterial gradient in pigs.

DETAILED DESCRIPTION

We turn now to the first embodiment of the invention which is directed to a method for preparing a stable iron nitrosylated hemoglobin which converts to SNO-hemoglobin when introduced into the bloodstream, comprising the step of reacting inorganic nitrite with deoxyhemoglobin at a mole ratio of inorganic nitrite to deoxhemoglobin (on a hemoglobin basis) ranging from 1:10 to 1:1000 to form iron nitrosyl hemoglobin.

The deoxyhemoglobin can be provided by deoxygenating hemoglobin or by deoxygenating red blood cells, e.g., by sparging hemoglobin or red blood cells with an inert gas, until less than 50% of the oxygen that normally is there, is present in the hemoglobin or red blood cells. The inert gas can be, for example, argon or nitrogen. The reaction is readily carried out at temperatures ranging from 4 to 37° C. and is conveniently carried out at room temperature, but may be carried out in the body (at body temperature). The inorganic nitrite is any inorganic nitrite which is soluble in a solvent together with the hemoglobin. The inorganic nitrite can be, for example, sodium or potassium nitrite. A solvent for the reaction is any solvent which does not inactivate hemoglobin from performing its physiological function and can be, for example, HEPES or 10 mm sodium phosphate buffer (pH 7.4). The iron nitrosyl hemoglobin contains NO bound to heme of hemoglobin β-subunit in very active state and is readily converted to SNO-hemoglobin in the body by the respiratory system. The SNO-hemoglobin has vasodilator activity and antiplatelet activity and by formation in the body is functional for these purposes despite being unstable, that is does not survive storage. Thus, the reaction of the first embodiment creates a molecule which on delivery into the body or formation in the body is endowed with vasodilator activity and as a result is useful to mitigate the increased morbidity and mortality risks normally associated with transfusion of blood substitute or red blood cells when used for or in conjunction with said transfusion.

We turn now to the second embodiment of the invention which is directed a method of blood product transfusion into a human patient in need of blood product transfusion, comprising the steps of co-incubating inorganic nitrite and blood substitute or red blood cells, comprising deoxygenated hemoglobin, at an initial mole ratio of nitrite to deoxygenated hemoglobin ranging from 1:10 to 1:1000, to form blood substitute or red blood cells product, containing iron nitrosyl hemoglobin, and transfusing the product containing iron nitrosyl hemoglobin into the patient.

The co-incubation is preferably carried out, for example, by admixing solution of inorganic nitrite in saline or other physiological buffer containing from 1 μM to 1 mM inorganic nitrite, with blood substitute or red blood cells, comprising deoxygenated hemoglobin, at an initial mole ratio of nitrite to deoxygenated hemoglobin ranging from 1:10 to 1:1000, e.g., 1:100 to 1:500, and mixing, for example, for 10 minutes to 1 hour, while maintaining the temperature at 4 to 37° C., preferably at body temperature.

Deoxygenation of the blood substitute or red blood cells to provide blood substitute or red blood cells, comprising deoxygenated hemoglobin, can be carried out, for example, by sparging the blood substitute or red blood cells with an inert gas, e.g., argon or nitrogen.

The inorganic nitrite is any that is soluble in and compatible with, that is does not degrade, the deoxygenated hemoglobin, and can be, for example, sodium nitrite or potassium nitrite.

The iron nitrosyl hemoglobin formed by the co-incubation is transformed in the body by the respiratory system to form SNO-hemoglobin which causes vasodilation to counter blood vessel constriction associated with conventional blood product transfusions.

The patient in need of blood product transfusion is a patient who has lost or is losing blood or one in need of removal of waste products of the body in case of failure of renal functioning or needs removal of toxic substance from blood in the case of poisoning or in need of red blood cells or hemoglobin to treat any disease associated with impairment of nitric oxide or oxygen, e.g., angina or stroke.

Transfusion is carried out at rates and over times as is conventional, e.g., 1 unit of blood substitute or red blood cells in 4 hours or less using an 18-gauge need or larger, e.g., transfusing said 1 unit in a time period of 30 minutes to 2 hours.

The activity of the blood substitute or red blood cells product can be potentiated by co-incubation of the product with glutathione or other thiol.

We turn now to the third embodiment of the invention herein which is directed to a method of blood product transfusion into a human patient in need of a blood product transfusion, with decreased mortality or morbidity risk from the transfusion compared to a conventional transfusion, comprising the steps of co-infusing blood substitute or red blood cells at the rate of 1 to 1000 cubic centimeters per hour and inorganic nitrite at the rate of 0.01 to 10 micromoles per minute, e.g., at the rate of 0.1 to 2 micromoles per minute.

The patients are the same as those for the second embodiment.

The inorganic nitrites are the same as those for the second embodiment and are used in the form of aqueous solutions, e.g., in saline or phosphate buffered saline, at concentrations ranging from 1 μM to 1 mM.

The transfusion of blood substitutes or red blood cells can be carried out as conventionally.

The transfusion of the nitrite solution is readily carried out at rates to provide the micromoles per minute of nitrite set forth above consistent with conventional blood substitute and red blood cell transfusion rates.

The reactions of the first embodiment are provided in the third embodiment because the infused nitrite encounters hemoglobin in the circulation system at very low-$PO_2$ so that deoxygenated hemoglobin is present and iron nitrosyl hemoglobin is formed in the circulation system which in turn is converted by the respiratory system to SNO-hemoglobin which provides the vasodilation and antiplatelet formations associated therewith.

We turn now to the fourth embodiment of the invention herein which is directed to stored whole blood, stored blood substitute, stored red blood cells, stored blood hemoglobin or combination thereof in admixture with nitric oxide or after inorganic nitrite pretreatment, for use at a later time, and to a method of providing composition for transfusion for use at a later time, comprising storing composition comprising whole blood, blood substitute, red blood cells, blood hemoglobin or combination of two or more thereof in admixture with nitric oxide or after inorganic nitrite pretreatment, to preserve function and any red blood cells. The pretreatment referred to corresponds to the incubation of the second embodiment and comprises incubating inorganic nitrite with whole blood, blood substitute, red blood cells, blood hemoglobin or combination of two or more thereof, comprising deoxygenated hemoglobin, the mole ratio of nitrite to deoxygenated hemoglobin ranging from 1:10 to 1:1000, to form composition containing iron nitrosyl hemoglobin. The incubation conditions and inorganic nitrites are those described for the second embodiment. The storage can be under the same conditions and with the same preservatives as are conventional. Whole blood or red blood cells preserved with citrate-phosphate-dextrose-adenine presently may be stored for 35 days and red blood cells presently may be stored for 42 days if adenine-saline preservative solution is added. The invention herein allows increase in these storage periods by at least 10%.

We turn now to the fifth embodiment of the invention herein which is directed to a method of treating a patient in need of nitric oxide therapy, comprising administering to the patient a red blood cells or blood hemoglobin based therapeutic obtained by incubating red blood cells or blood hemoglobin, comprising deoxygenated hemoglobin, with inorganic nitrite, the mole ratio of nitrite to deoxygenated hemoglobin ranging from 1:10 to 1:1000, whereby the therapeutic contains iron nitrosyl hemoglobin. The incubation conditions and inorganic nitrites are those described for the second embodiment. The treatment repletes nitric oxide independently of red blood cell component. Note that it is known that NO improves oxygen delivery capability of red blood cells and membrane function. The administration of the fifth embodiment of the invention herein, can be used, for example, to treat ischemia, e.g., myocardial ischemia.

Support for and elements of the invention are provided in a manuscript titled "NO interaction with oxidized hemes in human hemoglobin: routes to SNO-hemoglobin formation with preferential reactivity within the β-subunits." which is part of U.S. Provisional Patent Application No. 60/432,616, the whole of which is incorporated herein by reference. The manuscript indicates that inorganic nitrite can be employed to affix nitric oxide on hemes of hemoglobin and form iron nitrosyl hemoglobin which upon delivery into the body is endowed with vasodilator activity by virtue of being oxygenated by the respiratory system to form SNO-hemoglobin.

The invention herein is supported by the following background examples and is illustrated by the following working examples.

Background Example 1

As a model for reaction between ferric hemes and nitric oxide, the reductive nitrosylation of human methemoglobin was examined. Solutions of methemoglobin in 100 mM HEPES or 10 mM sodium phosphate buffer, pH 7.4, were prepared from human hemoglobin $A_0$ (Apex Bioscience, NC) and HEPES or sodium phosphate buffer, pH 7.4, as described in Gow, A. J., et al, Proc. Natl. Acad. Sci. USA 96, 9027 (1999). Reductive nitrosylation reactions were conducted by adding sodium nitrite to the methemoglobin solution at $[NO]_0$/[heme] mole ratios varying nominally from 0.05 to 0.75 (where $[NO]_0$ is the initial concentration of the added NO in the methemoglobin solution). Solutions were mixed by vortexing immediately upon aliquot addition. The protein concentration was kept in excess of 75 μM in all experiments to avoid dissociation of hemoglobin into dimers, and below 250 μM to maintain solution ideality. SNO-hemoglobin was determined to be a reaction product.

Background Example 2

Nitric oxide (NO) or sodium nitrite were incubated with packed deoxygenated red blood cells at 1:250 (NO or $NO_2^-$/hemoglobin) mole ratios in buffered saline at a concentration of deoxygenated red blood cell hemes of approximately 5 mM, for 15 minutes at room temperature.

Deoxygenation of the red blood cells was carried out by degassing with argon.

Direct measurements of the products resulting from incubation of NO or $NO_2^-$ with deoxygenated red blood cells show the products contain iron nitrosyl hemoglobin. The resulting product constituted blood substitute (Hct 30) and 50 cc of it was transfused four separate times into swine for a total of 1 unit (200 cc) of blood substitute. After each injection, the change in alveolar-arterial gradient in vivo was followed for 30 minutes and the means for 4 injections for control, NO incubation and $NO_2^-$ incubation were plotted and results are shown in FIG. 1 (n=4 at each point). Negative values reflect improvements in pig oxygenation. As shown in FIG. 1, both NO and nitrite treated deoxygenated red blood cells produced improvements in lung function as compared to control red blood cells which slightly impaired lung function (See 5 minute point). For the 10 minute point for nitric oxide and nitrite, p<0.01 compared to control.

Example I

Reactions with nitrite were conducted by mixing oxyhemoglobin solutions (about 4 mM in hemes) with sodium nitrite at about 100:1 heme:nitrite mole ratios. The solutions were allowed to stand at room temperature for minutes to hours, then deoxygenated by sparging with argon. Samples were withdrawn just before and just after deoxygenation for product characterization. The products before and after deoxygenation differ in that the product after deoxygenation contains iron nitrosyl hemoglobin. Oxidation of the product after reaction was carried out in about 2 mM solutions with an excess of potassium ferricyanide. The result was production of SNO-hemoglobin.

Example II

Sodium nitrite is incubated at room temperature for 15 minutes with packed deoxygenated red blood cells. The product is shown to contain iron nitrosyl hemoglobin.

A 67 year old with severe coronary disease is in a motor vehicle accident and therefore requires a blood transfusion. His hematocrit is 24. He is given 2 units of blood and his blood pressure rises 10 mm Hg. The patient experiences chest pain. An additional transfusion is recommended for continued blood loss. Nitrite pretreated red blood cells as described in the above paragraph are given without increase in blood pressure and the chest pain resolves. The same result is obtained even though the nitrite pretreated red blood cells are stored with preservative for 10% longer than is currently allowed.

Example III

The same scenario is present as in Example II but sodium nitrite in solution in phosphate buffered saline infusion at 1 micromole per minute is begun after which red blood cell transfusion is given without adverse effect.

Example IV

A 75-year old male with angina and a hematocrit of 40, receives an infusion of 100 cc nitrite pretreated red blood cells (pretreated as described in Example II) which does not change the oxygen carrying capacity of his blood but nevertheless resolves the angina.

VARIATIONS

Variations will be obvious to those skilled in the art. Therefore, the scope of the invention is defined by the claims.

What is claimed is:

1. A method of blood product transfusion into a human patient in need of a blood product transfusion, comprising the steps of co-administering a deoxygenated hemoglobin containing blood substitute and inorganic nitrite into the patient via infusion, wherein the inorganic nitrite is infused at a rate of 0.01 to 10 micromoles per minute, and the deoxygenated hemoglobin containing blood substitute is infused at a rate of 1 to 1000 cubic centimeters per hour.

2. The method of claim 1, wherein said patient is a patient who:
   a) has lost or is losing blood;
   b) is in need of removal of waste products of the body; or
   c) is in need of removal of a toxic substance.

3. The method of claim 1, wherein said patient is a patient in need of hemoglobin to treat angina or stroke.

4. The method of claim 1, wherein said inorganic nitrite is sodium nitrite or potassium nitrite.

5. The method of claim 1, wherein said inorganic nitrite is in the form of an aqueous solution.

6. The method of claim 5, wherein said aqueous solution is saline or phosphate buffered saline.

7. The method of claim 5, wherein said aqueous solution comprises inorganic nitrite at 1 μM to 1 mM.

* * * * *